United States Patent
Li et al.

(10) Patent No.: US 7,074,556 B2
(45) Date of Patent: **\*Jul. 11, 2006**

(54) CDNA SYNTHESIS IMPROVEMENTS

(75) Inventors: Wu Bo Li, North Potomac, MD (US);
Joel A. Jessee, Mt. Airy, MD (US);
Christian E. Gruber, Frederick, MD (US)

(73) Assignee: Invitrogen Corporation, Carlsbad, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/515,513

(22) Filed: Feb. 29, 2000

(65) Prior Publication Data

US 2002/0028447 A1 Mar. 7, 2002

Related U.S. Application Data

(60) Provisional application No. 60/122,395, filed on Mar. 2, 1999.

(51) Int. Cl.
*C12Q 1/68* (2006.01)

(52) U.S. Cl. ............... 435/6; 435/5; 435/6; 435/15; 435/91.1; 435/91.2; 435/68; 435/70; 530/350; 530/351; 530/324

(58) Field of Classification Search ............... 435/6, 435/5, 15, 91.1, 91.2, 68, 70; 530/351, 324, 530/350
See application file for complete search history.

(56) References Cited

U.S. PATENT DOCUMENTS

| | | | | |
|---|---|---|---|---|
| 4,748,233 A | * | 5/1988 | Sloma | 530/351 |
| 4,889,818 A | | 12/1989 | Gelfand et al. | 435/194 |
| 4,965,188 A | | 10/1990 | Mullis et al. | 435/6 |
| 5,219,989 A | | 6/1993 | Sonenberg et al. | 530/350 |
| 5,244,797 A | | 9/1993 | Kotewicz et al. | 435/194 |
| 5,338,671 A | * | 8/1994 | Scalice et al. | 435/91.2 |
| 5,374,553 A | | 12/1994 | Gelfand et al. | 435/252.3 |
| 5,405,776 A | | 4/1995 | Kotewicz et al. | 435/252.33 |
| 5,587,287 A | | 12/1996 | Scalice et al. | 435/6 |
| 5,595,895 A | | 1/1997 | Miki et al. | 435/172.3 |

(Continued)

FOREIGN PATENT DOCUMENTS

| | | |
|---|---|---|
| WO | WO 96/10640 | 4/1996 |
| WO | WO 98/08865 | 3/1998 |
| WO | WO 98/44161 A1 | 10/1998 |
| WO | WO 98/45311 | 10/1998 |
| WO | WO 98/47921 | 10/1998 |
| WO | WO 98/51699 | 11/1998 |

OTHER PUBLICATIONS

Fuchs, B. et al., "High Temperature cDNA Synthesis by AMV Reverse Transcriptase Improves the Specificity of PCR," *Molecular Biotechnology* 12:237–240, Humana Press (1999).

(Continued)

*Primary Examiner*—Braley L. Sisson
(74) *Attorney, Agent, or Firm*—Sterne, Kessler, Goldstein & Fox PLLC

(57) ABSTRACT

The present invention generally relates to methods of making cDNA molecules and cDNA libraries. The invention also relates to cDNA molecules and cDNA libraries produced according to these methods, as well as to vectors and host cells containing such cDNA molecules and libraries. The invention also relates to kits for making the cDNA molecules and libraries of the invention.

24 Claims, 6 Drawing Sheets

U.S. PATENT DOCUMENTS

| | | | |
|---|---|---|---|
| 5,668,005 A | | 9/1997 | Kotewicz et al. ............ 435/194 |
| 5,824,875 A | * | 10/1998 | Ranu ............................ 800/205 |
| 5,989,819 A | * | 11/1999 | Odawara ......................... 435/6 |
| 6,013,488 A | | 1/2000 | Hayashizaki .............. 435/91.51 |
| 6,063,608 A | | 5/2000 | Kotewicz et al. ............ 435/194 |
| 6,096,877 A | * | 8/2000 | Vlasuk et al. .............. 536/23.5 |
| 6,103,473 A | * | 8/2000 | Copeland et al. ............... 435/6 |
| 6,143,528 A | | 11/2000 | Hayashizaki ............... 435/91.1 |
| 6,187,544 B1 | | 2/2001 | Bergsma et al. ................ 435/6 |

OTHER PUBLICATIONS

Gerard, G. et al., "Reverse Transcriptase: The Use of Cloned Moloney Murine Leukemia Virus Reverse Transcriptase to Synthesize DNA from RNA," *Molecular Biotechnology* 8:61–77, Humana Press (1997).

Nathan, M. et al., "Optimizing Long RT–PCR," *Focus* 17:78–80, Life Technologies, Inc. (1995).

Sambrook, J. et al., "Amplification of DNA Generated by Reverse Transcription of mRNA," *Molecular Cloning: A Laboratory Manual*. Second Edition, 2:14.20–14.21, Cold Spring Harbor Laboratory Press (1989).

Sambrook, J. et al., "Reverse Transcriptase (RNA–dependent DNA Polymerase)," *Molecular Cloning: A Laboratory Manual*. Second Edition, 1:5.52–5.55, Cold Spring Harbor Laboratory Press (1989).

Sambrook, J. et al., "Synthesis of the First Strand of cDNA," *Molecular Cloning: A Laboratory Manual*. Second Edition, 2:8.11–8.20, Cold Spring Harbor Laboratory Press (1989).

Schwabe, W. et al., "ThermoScript™ RT, a New Avian Reverse Transcriptase for High–Temperature cDNA Synthesis to Improve RT–PCR," *Focus* 20:30–33, Life Technologies, Inc. (1998).

Yu, H. and Goodman, M.F., "Comparison of HIV–1 and Avian Myeloblastosis Virus Reverse Transcriptase Fidelity on RNA and DNA Templates," *Journal of Biological Chemistry* 267:10888–10896, The American Society for Biochemistry and Molecular Biology, Inc. (1992).

GIBCO BRL Instruction Manual for SUPERSCRIPT™ First–Strand Synthesis System for RT–PCR. Catalog No. 11904–018. Life Technologies, Inc. (2000).

GIBCO BRL Instruction Manual for SUPERSCRIPT™ Preamplification System for First Strand cDNA Synthesis. Catalog No. 18089–011. Life Technologies, Inc. (2000).

Carninci, P. et al., "High–Efficiency Full–Length cDNA Cloning by Biotinylated CAP Trapper," *Genomics* 37:327–336, Academic Press, Inc. (1996).

Chenchik, A. et al., "Full–Length cDNA Cloning and Determination of mRNA 5' and 3' Ends by Amplification of Adaptor–Ligated cDNA," *BioTechniques* 21:526–534, Eaton Publishing Co. (1996).

DeVico, A. et al., "Purification and partial characterization of equine infectious anemia virus reverse transcriptase," *Virology* 185:387–394, abstract only, from NCBI PubMed, PMID 1718086 (1991).

"Enzymatic Amplification of RNA by PCR," in: *Current Protocols in Molecular Biology Supplement 17*, Ausubel, F., et al., eds., John Wiley and Sons, Inc., New York, New York, pp. 15.4.1–15.4.4 (1992).

Gerard, G., "Reverse Transcriptase: A Historical Perspective," *Focus* 20:65–67 (Sep. 1998).

Kaufman, P.B. et al., *Handbook of Molecular and Cellular Methods in Biology and Medicine*, CRC Press, Boca Raton, FL (1995), pp. 444–467.

Kotewicz, M.L. et al., "Isolation of cloned Moloney murine leukemia virus reverse trancriptase lacking ribonuclease H activity," *Nucl. Acids Res.* 16:265–277 (1988).

Lovett M. et al., "The construction of full length cDNA libraries by conventional methods and a novel double capture technique," *The American Journal of Human Genetics Suppl. to 63*:A253, Abstract No. 1456 (Oct., 1998).

Mierendorf, K. and Novy, R., "A High Efficiency cDNA Cloning Vector for Protein Expression, Purification and Substractive Probe Synthesis," *inNovations*, Nova Gen, Inc., No. 3, pp. 1–3 (1995).

Mizuno, Y. et al., "Increased specificity of reverse transcription priming by trehalose and oligo–blockers allows high–efficiency window separation of mRNA display," *Nucl. Acids Res.* 27:1345–1349 (1999).

Morris, B. et al., "A Novel Strategy for Directional Cloning of Random Primed cDNA," *inNovations*, Nova Gen, Inc., No. 3, pp. 1–8 (1995).

Saiki, R.K. et al., "Primer–Directed Enzymatic Amplification of DNA with a Thermostable DNA Polymerase," *Science* 239:487–491 (1988).

Soltis, D.A. and Skalka, A.M., "The $\alpha$ and $\beta$ chains of avian retrovirus reverse transcriptase independently expressed in *Escherichia coli*: Characterization of enzymatic activities," *Proc. Natl. Acad. Sci. USA* 85:3372–3376 (1988).

International Search Report for International Application No. PCT/US00/05138, mailed May 25, 2000.

"Enzymatic Amplification of RNA by PCR," in: *Current Protocols in Molecular Biology Supplement 17*, Ausubel, F., et al., eds., John Wiley and Sons, Inc., New York, New York, pp. 15.4.1–15.4.4 (1992).

Zhang, J. and Byrne, C.D., "Differential priming of RNA templates during cDNA synthesis markedly affects both accuracy and reproducibility of quantitative competitive reverse–transcriptase PCR," *Biochem. J.* 337:231–241, Biochemical Society/Portland Press (Jan. 1999).

Copy of Supplementary Partial European Search Report for European Patent Application No. 00912051, mailed Nov. 19, 2004.

Chou, Q., et al., "Prevention of pre–PCR mis–priming and primer dimerization improves low–copy–number amplifications," *Nucl. Acids Res.* 20:1717–1723, Oxford University Press (1992).

* cited by examiner

M 1 2 3 4 5

SEQUENCE LISTING

<160> NUMBER OF SEQ ID NOS: 1

<210> SEQ ID NO 1
<211> LENGTH: 54
<212> TYPE: DNA
<213> ORGANISM: Artificial Sequence
<220> FEATURE:
<223> OTHER INFORMATION: Description of Artificial Sequence: primer

<400> SEQUENCE: 1
gactagttct agatcgcgag cggccgccct tttttttttt tttttttttt tttt         54

CDNA SYNTHESIS IMPROVEMENTS

CROSS REFERENCE TO RELATED APPLICATIONS

This application claims the benefit, under 35 U.S.C. § 119(e), of U.S. Provisional Application No. 60/122,395, filed on Mar. 2, 1999, which is fully incorporated by reference herein.

BACKGROUND OF THE INVENTION

The present invention relates to the field of molecular and cellular biology. The invention generally relates to methods of synthesizing cDNA. More specifically, the present invention relates to methods of increasing the average cDNA insert size and more particularly, to increasing the percentage of full-length cDNA present within cDNA libraries. Thus, the present invention provides improved cDNA libraries useful in gene discovery.

In examining the structure and physiology of an organism, tissue or cell, it is often desirable to determine its genetic content. The genetic framework of an organism is encoded in the double-stranded sequence of nucleotide bases in the deoxyribonucleic acid (DNA) which is contained in the somatic and germ cells of the organism. The genetic content of a particular segment of DNA, or gene, is only manifested upon production of the protein which the gene encodes. In order to produce a protein, a complementary copy of one strand of the DNA double helix (the "coding" strand) is produced by polymerase enzymes, resulting in a specific sequence of ribonucleic acid (RNA). This particular type of RNA, since it contains the genetic message from the DNA for production of a protein, is called messenger RNA (mRNA).

Within a given cell, tissue or organism, there exist many mRNA species, each encoding a separate and specific protein. This fact provides a powerful tool to investigators interested in studying genetic expression in a tissue or cell. mRNA molecules may be isolated and further manipulated by various molecular biological techniques, thereby allowing the elucidation of the full functional genetic content of a cell, tissue or organism.

A common approach to the study of gene expression is the production of complementary DNA (cDNA) clones. In this technique, the mRNA molecules from an organism are isolated from an extract of the cells or tissues of the organism. This isolation often employs solid chromatography matrices, such as cellulose or agarose, to which oligomers of thymidine (T) have been complexed. Since the 3' termini on most eukaryotic mRNA molecules contain a string of adenosine (A) bases, and since A binds to T, the mRNA molecules can be rapidly purified from other molecules and substances in the tissue or cell extract. From these purified mRNA molecules, cDNA copies may be made using the enzyme reverse transcriptase (RT) or DNA polymerases having RT activity, which results in the production of single-stranded cDNA molecules. The single-stranded cDNAs may then be converted into a complete double-stranded DNA copy (i.e., a double-stranded cDNA) of the original mRNA (and thus of the original double-stranded DNA sequence, encoding this mRNA, contained in the genome of the organism) by the action of a DNA polymerase. The protein-specific double-stranded cDNAs can then be inserted into a vector, which is then introduced into a host bacterial, yeast, animal or plant cell, a process referred to as transformation or transfection. The host cells are then grown in culture media, resulting in a population of host cells containing (or in many cases, expressing) the gene of interest or portions of the gene of interest.

This entire process, from isolation of mRNA to insertion of the cDNA into a vector (e.g., plasmid, viral vector, cosmid, etc.) to growth of host cell populations containing the isolated gene or gene portions, is termed "cDNA cloning." If cDNAs are prepared from a number of different mRNAs, the resulting set of cDNAs is called a "cDNA library," an appropriate term since the set of cDNAs represents a "population" of genes or portions of genes comprising the functional genetic information present in the source cell, tissue or organism. Genotypic analysis of these cDNA libraries can yield much information on the structure and function of the organisms from which they were derived.

The ability to increase the total amount of cDNA produced, and more particularly to produce a cDNA libraries having an increase in the average size of the cDNA molecules and/or to produce cDNA libraries having an increase in the percentage of full-length cDNA molecules would provide a significant advance in cDNA library construction. Specifically, such advances would greatly improve the probability of finding full-length genes of interest.

Ideally, synthesis of a cDNA molecule initiates at or near the 3' termini of the mRNA molecules. Priming of cDNA synthesis at the 3' termini at the poly A tail using an oligo(dT) primer ensures that the 3' message of the mRNAs will be represented in the cDNA molecules produced. Priming which occurs within the mRNA molecules (internal priming) results in synthesis of cDNA molecules which do not contain the full-length message for the genes of interest. That is, internal priming results in truncated cDNA molecules which contain only a portion of the gene or genes of interest. Typically, internal priming causes a loss of the 3' sequences from the message population. Thus, internal priming lowers the total amount of cDNA produced, decreases the average insert size of cDNA molecules for a cDNA library and/or decreases the percentage of full-length cDNA molecules in a given cDNA library. Sequencing analysis has indicated that many eukaryotic mRNAs have internal poly adenylation stretches which may serve as a priming site when an oligo(dT) primer is used for first strand cDNA synthesis with reverse transcriptase. Moreover, research has shown that some mRNAs can have as many as 16 internal priming sites (Lovett, M., et al., The construction of full-length cDNA libraries by conventional methods and a novel double capture technique, University of Texas Southwestern Medical Center, Dallas, Tex., presented at the 48$^{th}$ Annual Meeting held by The American Society of Human Genetics, Oct. 27–31, 1998, Denver, Colo.). Thus, internal priming of the primer to such internal poly A sequences may adversely affect cDNA synthesis.

The present invention alleviates, prevents, reduces or substantially reduces internal priming thereby providing improvements in cDNA and cDNA library construction. Accordingly, the present invention greatly facilitates gene discovery by providing cDNA libraries containing a greater percentage of full-length genes.

The present invention therefore relates to synthesizing a cDNA molecule or molecules from an mRNA template or population of mRNA templates under conditions sufficient to increase the total amount of cDNA produced, increase the length of the cDNA molecules produced, and/or increase the amount or percentage of full-length cDNA molecules produced. In accordance with the invention, any conditions which inhibit, prevent, reduce or substantially reduce internal priming may be used. Such conditions preferably include but are not limited to optimizing primer concentrations, optimizing reaction temperatures and/or optimizing primer length or specificity. Such result may also be accomplished in accordance with the invention by optimizing the reverse transcription reaction, preferably by inhibiting or preventing reverse transcription until optimum or desired reaction conditions are achieved.

Conventional methods for constructing cDNA libraries use a molar ratio of oligo(dT) primer/mRNA template of 15:1 for first strand cDNA synthesis. The use of such excess amounts of oligo(dT) primer allows internal priming of one or more primers to one or more of the mRNA templates in the reaction. According to a preferred aspect of the present invention, the amount of oligo(dT) primer is reduced for synthesis of first strand cDNA to inhibit, prevent, reduce or substantially reduce internal priming. Preferred molar ratios of primer to template range from about 12:1; 10:1; 9:1; 8:1; 7:1; 6:1; 5:1; 4:1; 3:1; 2:1; 1:1; 1:2; 1:3; 1:4; 1:5; 1:6; 1:7; 1:8; 1:9; 1:10 and 1:12. Preferably, molar ratios of primer (e.g., oligo(dT)) to template (e.g., mRNA) range from about 5:1 to about 1:20, although lower molar ratios of primer to template may be used in accordance with the invention. Specifically, molar ratios of primer to template may be below about 1:10; 1:15; 1:20; 1:25; 1:50; 1:75; and 1:100. Preferably, ranges of molar ratios are below about 5:1; 4:1; 3:1; 2:1; 1:1; 1:2; 1:3; 1:4; and 1:5. Most preferably, ratios of primer to template range from about 10:1 to 1:10; 5:1 to 1:10; 4:1 to 1:10; 3:1 to 1:10; 2.5:1 to 1:10; 2:1 to 1:10; 1.5:1 to 1:10; and 1:1 to 1:10. The optimum ratios of primer to template may vary depending on the primer, mRNA, reverse transcription enzyme and reaction conditions (annealing temperature, buffering salts, etc.). The desired primer to template ratios can be readily determined by one skilled in the art.

In conventional methods of cDNA library construction, annealing or hybridizing primer to template is not carried out at a temperature which prevents, inhibits, reduces or substantially reduces internal priming. Typically, the mixture (e.g., mRNA and oligo(dT) primer) is chilled on ice after denaturation or heating. This process typically causes annealing or hybridization of the primer to internal sites. According to a preferred aspect of the present invention, the temperature during the annealing or hybridization between the primer and the template is maintained so that internal priming is inhibited, prevented, reduced or substantially reduced. In accordance with the invention, such a result is accomplished by carrying out primer annealing or hybridization at higher temperatures. Such conditions may also reduce the formation of mRNA secondary structures during cDNA synthesis. Preferably, temperatures for annealing or hybridizing primers to the templates range from about 10° C. to about 90° C.; more preferably about 10° C. to about 80° C.; still more preferably about 20° C. to about 75° C.; more preferably about 25° C. to about 75° C.; still more preferably about 30° C. to about 65° C.; still more preferably about 37° C. to about 60° C.; still more preferably about 40° C. to about 60° C.; still more preferably about 45° C. to about 60° C.; still more preferably about 45° C. to about 55° C.; and most preferably about 45° C. to about 65° C. The temperature used may vary depending on the type and amount of primer and template and depending on the temperature optimum of the reverse transcription enzyme. The optimum temperature or temperature ranges can be readily determined by one skilled in the art.

Conventional methods for cDNA synthesis typically requires the use of oligo(dT) primers of a particular length (12–18 bases or mer). Such primer length, however, lowers specificity of the primer thereby allowing internal priming. Thus, the invention also relates to increasing specificity of the primers to prevent, inhibit, reduce or substantially reduce internal priming. In a preferred aspect, primer specificity is increased by increasing the length of the primer. Thus, for cDNA synthesis, longer oligo(dT) primers may be used in accordance with the invention. Preferably, primer length ranges from about 20 to about 100 bases, about 20 to about 75 bases, about 20 to about 60 bases, and about 20 to about 50 bases; more preferably about 20 to about 45 bases; more preferably about 20 to about 40 bases; and most preferably about 25 to about 35 bases. In a preferred aspect, the length of the primers are greater than 19 bases; more preferably greater than about 20 bases; more preferably greater than about 25 bases; and still more preferably greater than about 30 bases. Such primer lengths refer to the length of the primers which anneal or hybridize to the template Optimum length and content (nucleotide sequence) of the primers may vary depending on the type of template, the desired reaction conditions, and the reverse transcription enzyme. In accordance with the invention, additional sequences and/or modified nucleotides may be included in the primers of the invention. For example, additional sequences (which do not necessarily anneal or hybridize to the template) may be included in the primers of the invention to assist in cDNA synthesis including sequences comprising one or more restriction endonuclease sites, one or more derivative nucleotides (e.g., hapten containing nucleotides such as biotinylated nucleotides), and the like. The type and length of the primers used in accordance with the invention can be readily determined by one or more skilled in the art.

Conventional cDNA synthesis methods do not control or vary activity of the reverse transcription enzyme to optimize the reverse transcription reaction. In accordance with the invention, the activity of the reverse transcriptase is preferably controlled to start synthesis at a desired time in the reaction. In a preferred aspect, reverse transcriptase activity is inhibited or prevented until optimum or desired reaction conditions are achieved. Such a result is accomplished in accordance with the invention by the use of inhibitors (such as antibodies or antibody fragments) which inhibit reverse transcriptase activity. Such reverse transcriptase inhibitors prevent or inhibit reverse transcriptase activity at low temperatures such that internal priming is prevented, inhibited, reduced or substantially reduced. In accordance with the invention, such inhibitors preferably prevent reverse transcriptase activity below 35° C., below 40° C., below 45° C., below 50° C., below 55° C., below 60° C., below 65° C., below 70° C., below 75° C., below 80° C., below 85° C. and below 90° C. Depending on the thermostability of the enzyme having reverse transcriptase activity, the inhibitor may be designed to inhibit activity of the enzyme at a point at or near the temperature optimum for the enzyme of interest. Preferably, the inhibitor is inactivated at a temperature below or near the temperature optimum of the enzyme used, thereby allowing reverse transcription to take place. Thus, the invention generally relates to the use of reverse transcriptase inhibitors in cDNA synthesis. The type and amount of inhibitor may vary depending on the type and amount of reverse transcription enzyme and depending on the reaction conditions to be used. The type of inhibitor and conditions used with such inhibitor can be readily determined by one of ordinary skill in the art.

In accordance with the invention, any one or a combination of the above improvements to cDNA synthesis may be used. Using any one or a combination of these improvements provides for improved first strand cDNA synthesis (e.g., more total cDNA, larger cDNA and/or more full-length cDNA). In accordance with the invention, the first strand cDNA molecules may be used as templates to make one or more double stranded nucleic acid molecules (e.g., double strand cDNA molecules) by incubating one or more of the first strand cDNA molecules produced by the methods of the invention under conditions sufficient to make one or more nucleic acid molecules complementary to all or a portion of the first strand cDNA molecules. Conditions for making double stranded nucleic acid molecules preferably include incubation with one or more components consisting of one or more DNA polymerases, one or more nucleotides, one or more buffering salts, and one or more primers. In another aspect of the invention, such conditions are modified to provide an increase in the total amount of double stranded cDNA produced, an increase in the length or size of the double stranded cDNA molecule produced, and/or an increase in percentage full-length double stranded cDNA molecule produced. Preferably, such conditions relate to optimization of ribonuclease (RNase) digestion after first strand cDNA synthesis. During first strand cDNA synthesis, if a full-length cDNA molecule complementary to the mRNA template is not made, a single stranded mRNA containing the cap structure will be present at the 5' end of the mRNA of the mRNA/cDNA hybrid. If a full-length cDNA is produced, a double stranded mRNA/cDNA hybrid is produced with no single stranded mRNA present. Preferably, such digestion conditions are optimized so that the single stranded mRNA of the mRNA/cDNA double stranded molecules formed during first strand cDNA synthesis is subject to RNase digestion. In this manner, cap structure from mRNA/cDNA hybrids which are not full-length are removed while full-length mRNA/cDNA hybrids will retain the cap structure. Thus, cap capture can be used to select for full-length molecules and select against molecules which are not full-length. In a preferred aspect, the conditions are such that the single stranded mRNA of the mRNA/cDNA hybrid is digested or degraded while the mRNA of the double stranded mRNA/cDNA hybrid is not degraded or not substantially degraded. Thus, such RNase digestion is conducted under conditions such that second strand synthesis is not substantially adversely affected. That is, second strand synthesis in accordance with the invention produces larger double stranded cDNA molecules compared to conventional techniques. Conventional RNase I conditions typically range from 25 u/µg to 40 u/µg mRNA at 37° C. and RNase A conditions typically are 1000 ng/µg mRNA at 37° C. Using conventional RNase digestion, the average size of double stranded cDNA molecules produced is about 200 bases. According to the present invention the average size of double stranded cDNA molecules produced is preferably greater than about 300 bases, greater than about 400 bases, greater than about 500 bases, greater than about 600 bases, greater than about 700 bases, greater than about 800 bases, greater than about 900 bases, greater than about 1 kilobase, greater than about 1.5 kilobases, and greater than about 2 kilobases. In one embodiment of the invention, the concentration of the ribonuclease, the type of ribonuclease and reaction conditions are optimized to improve double stranded cDNA synthesis in accordance with the invention. Preferred ribonucleases for use in ribonuclease digestions include ribonuclease A (RNase A) and/or ribonuclease I (RNase I). Generally, lower temperatures (about 4° C. to about 50° C.) and higher salt concentrations (about 5 mM to about 5 M) will assist in inhibiting or controlling RNase digestion in accordance with the invention. Salts used may include sodium chloride, potassium, chloride, magnesium chloride, sodium acetate etc. Additionally, lowering RNase amounts or concentrations may be used to accomplish the desired result. Such concentrations for RNase A may range from about 0.001 ng/µg mRNA to about 500 ng/µg of mRNA and for RNase I may range from about 0.001 u/µg mRNA to about 500 u/µg mRNA. The incubation temperature, RNase concentration and salt concentration may be readily determined by one skilled in the art. In a preferred aspect, concentration of the RNase A include ranges from 0.1 ng/µg mRNA to 10 ng/µg mRNA in TE buffer (10 mM Tris, pH 7.5, 1 mM EDTA) at 37° C. Alternatively, the concentration of the RNase A can include ranges from 0.1 ng/µg mRNA to 500 ng/µg mRNA in 10 mM Tris, pH 7.5 buffer containing 250 mM NaCl at 25° C. for 30 minutes. Preferably, concentration of the RNase I used ranges from 0.1 unit/µg mRNA to 1.0 unit/µg mRNA in 10 mM Tris-HCl (pH 7.5), 5 mM EDTA (pH 8.0), 200 mM sodium acetate at 37° C. Alternatively, the concentration of the RNase I can be used at ranges from 1.0 unit/µg mRNA to 100 units/µg mRNA in the same buffer at 25° C. for 30 minutes.

In another aspect, the invention relates to capture or binding of the cap structure (e.g., m$^7$GpppN) of the mRNA before, during or after first strand cDNA synthesis. Thus, the invention relates to selection of mRNA (before first strand synthesis) or mRNA/cDNA hybrids (after or during first strand synthesis) which have the cap structure in carrying out the methods of the invention. Such selection or capture may be accomplished with any cap binding molecule such as eIF4E, eIF4E peptides, eIF4E peptide fragments (see WO 98/08865) and antibodies or antibody fragments specific for cap structure. In a preferred aspect, selection of the cap structure is accomplished after first strand synthesis. More preferably, such cap capture occurs after ribonuclease digestion in accordance with the methods of the invention. For example, mRNA/cDNA hybrids subjected to ribonuclease digestion are captured and then used for second strand cDNA synthesis according to the invention.

Thus, the present invention is generally directed to methods of synthesizing nucleic acid molecules. The present invention is more specifically directed to methods of making one or more nucleic acid molecules, especially cDNA molecules or cDNA libraries, comprising mixing one or more nucleic acid templates (preferably mRNA, poly A RNA or a population of mRNA molecules) with at least one polypeptide having reverse transcriptase activity, and incubating the mixture under conditions sufficient to make one or more first nucleic acid molecules (e.g., first strand cDNA) complementary to all or a portion of the one or more nucleic acid templates.

In accordance with the invention, such conditions provide for an increased total amount of nucleic acid molecule (cDNA) produced, compared to conventional procedures which do not employ the improved modifications or conditions of the invention. The invention also provides for an increase of length or average size of the nucleic acid molecules (cDNA) produced and/or an increase in the percentage or amount of full-length nucleic acid molecules (cDNA) produced, compared to conventional procedures which do not employ the improved modifications or conditions of the invention. Determining the amount, length and full-length content of the cDNA produced can be determined by conventional techniques well known in the art and as described herein. The percentage or average percentages of full-length cDNA in cDNA libraries produced in accordance with the invention are preferably above about 15%, more preferably above about 20%, more preferably above about 25%, more preferably above about 30%, more preferably above about 40%, more preferably above about 50%, more preferably above about 60%, more preferably above about 70%, more preferably above about 80% and most preferably above about 90% Such full-length percentages are preferably determined by random selection of a portion of the clones of the cDNA library of interest (e.g., 100 to 1000 clones), sequencing the clones and comparing the sequences to known sequence data bases.

In preferred aspects of the invention, the improved results of the invention are preferably accomplished by one or a combination of modifications to the conditions for nucleic acid or cDNA synthesis. Such conditions preferably include modifications for improving first strand cDNA synthesis and/or improving second strand cDNA synthesis.

In a preferred aspect, the invention specifically relates to methods of making one or more double stranded cDNA molecules comprising incubating one or more mRNA molecules preferably a population of mRNA molecules) with one or more primers of the invention at temperatures and primer concentrations to prevent, inhibit, reduce or substantially reduce internal priming prior to or during first strand cDNA synthesis. Such reaction is preferably conducted in the presence of one or more inhibitors of reverse transcriptase activity in accordance with the invention. Ribonuclease digestion is preferably conducted before second strand cDNA synthesis and at ribonuclease concentrations sufficient to increase the length, amount and/or size of double stranded cDNA molecules produced during second strand synthesis. In accordance with the invention, cap capture is preferably accomplished during or after the ribonuclease digestion.

The invention is also directed to nucleic acid molecules and cDNA molecules or populations of cDNA molecules (single or double-stranded) produced according to the above-described methods and to vectors (particularly expression vectors) comprising these nucleic acid molecules and cDNA molecules. The invention also relates to host cells containing such cDNA molecules and/or vectors.

The invention is also directed to kits for use in the methods of the invention. Such kits can be used for making single or double-stranded nucleic acid molecules. The kits of the invention comprise a carrier, such as a box or carton, having therein one or more containers, such as vials, tubes, bottles and the like. Such kits may comprise at least one component selected from the group consisting of primers (preferably primers having higher specificity and most preferably oligo(dT) primers having a length equal to or greater than 20 bases), one or more polypeptides having reverse transcriptase activity (reverse transcriptases and DNA polymerases), one or more inhibitors of reverse transcription (e.g., antibodies and antibody fragments directed against polypeptides having RT activity), one or more cap binding molecules (e.g., antibodies or antibody fragments directed against cap structure), nucleic acid synthesis reaction buffers, one or more nucleotides, one or more vectors, and instructions for carrying out the methods of the invention.

The invention also relates to compositions for use in the invention or made while carrying out the methods of the invention. Such compositions may comprise at least one primer (e.g., oligo(dT) or derivatives thereof) and at least one template in a sample or reaction mixture in amounts or ratios in accordance with the invention. Such composition may further comprise one or more polypeptides having reverse transcriptase activity, one or more reverse transcription inhibitors (e.g., anti-RT antibodies or fragments thereof), one or more nucleotides, one or more cap binding molecules (e.g., anti-cap antibodies for fragments thereof), one or more buffering salts and the like. Such compositions may also be maintained at a temperature to avoid internal priming in accordance with the invention.

The compositions of the invention may also comprise amounts of ribonuclease in accordance with the invention. Such compositions may further comprise at least one component selected from one or more mRNA/cDNA hybrids, one or more nucleotides, one or more polypeptides having reverse transcriptase activity, one or more buffering salts, one or more cap binding molecules (e.g., anti-cap antibodies or fragments thereof) and the like.

The invention also relates to one or more antibodies (monoclonal and polyclonal) and fragments thereof for use in the methods, compositions and kits of the invention. Such antibodies, include anti-cap and/or anti-RT antibodies and antibody fragments Other preferred embodiments of the present invention will be apparent to one of ordinary skill in the art in view of the following drawings and description of the invention.

DETAILED DESCRIPTION OF THE PREFERRED EMBODIMENTS

Figure 1:
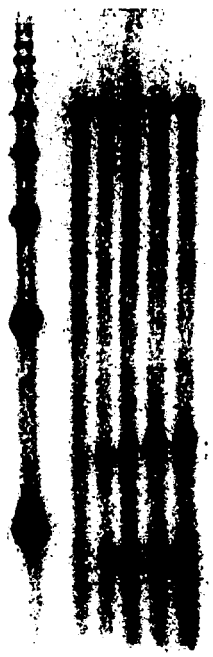
FIG. 1 is an autoradiograph of first strand cDNA synthesized with SuperScript™ II (SS II) RT at 45° C. with a ⅚ Kb template with molar ratios of oligo(dT)$_{25-30}$/mRNA of 1:1, 2.5:1, 5:1, 10:1, and 50:1.

Definitions:

In order to provide a clearer and consistent understanding of the specification and claims, including the scope to be given such terms, the following definitions are provided.

Internal priming as used herein refers to hybridization or annealing of one or more primers at one or more sites within one or more mRNA molecules other than at the poly A tail located at the 3' termini of the mRNA molecule.

Library as used herein refers to a set of nucleic acid molecules (circular or linear) which is representative of all or a portion or significant portion of the DNA content of an organism (a "genomic library"), or a set of nucleic acid molecules representative of all or a portion or significant portion of the expressed genes (a "cDNA library") in a cell, tissue, organ or organism. Such libraries may or may not be contained in one or more vectors.

Vector as used herein refers to a plasmid, cosmid, phagemid or phage DNA or other DNA molecule which is able to replicate autonomously in a host cell, and which is characterized by one or a small number of restriction endonuclease recognition sites at which such DNA sequences may be cut in a determinable fashion without loss of an essential biological function of the vector, and into which DNA may be inserted in order to bring about its replication and cloning. The vector may further contain one or more markers suitable for use in the identification of cells transformed with the vector. Markers, for example, include but are not limited to tetracycline resistance or ampicillin resistance. Such vectors may also contain one or more recombination sites, one or more termination sites, one or more origins of replication, and the like.

Primer as used herein refers to a single-stranded oligonucleotide that is extended by covalent bonding of nucleotide monomers during amplification or polymerization of a DNA molecule. Preferred primers for use in the invention include oligo(dT) primers or derivatives or variants thereof.

Oligonucleotide as used herein refers to a synthetic or natural molecule comprising a covalently linked sequence of nucleotides which are joined by a phosphodiester bond between the 3' position of the deoxyribose or ribose of one nucleotide and the 5' position of the deoxyribose or ribose of the adjacent nucleotide.

Template as used herein refers to double-stranded or single-stranded nucleic acid molecules which are to be amplified, synthesized or sequenced. In the case of a double-stranded molecules, denaturation of its strands to form a first and a second strand is preferably performed before these molecules may be amplified, synthesized or sequenced, or the double stranded molecule may be used directly as a template. For single stranded templates, a primer, complementary to a portion of the template is hybridized or annealed under appropriate conditions and one or more polymerases or reverse transcriptases may then synthesize a nucleic acid molecule complementary to all or a portion of said template. The newly synthesized molecules, according to the invention, may be equal or shorter in length than the original template.

Incorporating as used herein means becoming a part of a DNA and/or RNA molecule or primer.

Amplification as used herein refers to any in vitro method for increasing the number of copies of a nucleotide sequence with the use of a polymerase. Nucleic acid amplification results in the incorporation of nucleotides into a DNA and/or RNA molecule or primer thereby forming a new molecule complementary to a template. The formed nucleic acid molecule and its template can be used as templates to synthesize additional nucleic acid molecules. As used herein, one amplification reaction may consist of many rounds of replication. DNA amplification reactions include, for example, polymerase chain reactions (PCR). One PCR reaction may consist of 5 to 100 "cycles" of denaturation and synthesis of a DNA molecule.

Nucleotide as used herein refers to a base-sugar-phosphate combination. Nucleotides are monomeric units of a nucleic acid sequence (DNA and RNA). The term nucleotide includes ribonucleoside triphosphates ATP, UTP, CTG, GTP and deoxyribonucleoside triphosphates such as dATP, dCTP, dITP, dUTP, dGTP, dTTP, or derivatives thereof. Such derivatives include, for example, [αS]dATP, 7-deaza-dGTP, 7-deaza-dATP, and biotinylated or haptenylated nucleotides.

The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels.

Hybridization or annealing as used herein refers to base pairing of two complementary single-stranded nucleic acid molecules (RNA and/or DNA) to give a double-stranded molecule. As used herein, two nucleic acid molecules may be hybridized or annealed, although the base pairing is not completely complementary. Accordingly, mismatched bases do not prevent hybridization or annealing of two nucleic acid molecules provided that appropriate conditions, well known in the art, are used. In the present invention, the term hybridization or annealing preferably refers to hybridization of one or more primers (e.g., oligo(dT) or derivatives thereof) to one or more templates (e.g., mRNA).

Host cell as used herein refers to any prokaryotic or eukaryotic cell that is the recipient of a replicable expression vector or cloning vector. The terms "host" or "host cell" may be used interchangeably herein. For examples of such hosts, see Maniatis et al., "Molecular Cloning: A Laboratory Manual," Cold Spring Harbor Laboratory, Cold Spring Harbor, N.Y. (1982). Preferred prokaryotic hosts include, but are not limited to, bacteria of the genus Escherichia (e.g., E. coli), Bacillus, Staphylococcus, Agrobacter (e.g., A. tumefaciens), Streptomyces, Pseudomonas, Salmonella, Serratia, Caryophanon, etc. The most preferred prokaryotic host is E. coli. Bacterial hosts of particular interest in the present invention include E. coli strains K12, DH10B, DH5α, Stb12 and HB101, and others available from Life Technologies, Inc. Preferred eukaryotic hosts include, but are not limited to, fungi, fish cells, yeast cells, plant cells and animal cells. Particularly preferred animal cells are insect cells such as Drosophila cells, Spodoptera Sf9, Sf21 cells and Trichoplusa High-Five cells; nematode cells such as C. elegans cells; and mammalian cells such as COS cells, CHO cells, VERO cells, 293 cells, PERC6 cells, BHK cells and human cells.

Expression vector as used herein refers to a vector which is capable of enhancing the expression of a gene or portion of a gene which has been cloned into it, after transformation or transfection into a host cell. The cloned gene is usually placed under the control (i.e., operably linked to) certain control sequences such as promoter sequences. Such promoters include but are not limited to phage lambda $P_L$ promoter, and the E. coli lac, trp and tac promoters. Other suitable promoters will be known to the skilled artisan.

The nucleic acid templates suitable for reverse transcription according to the invention include any nucleic acid molecule or populations of nucleic acid molecules (preferably one or more RNA molecules (e.g., one or more mRNA molecules or poly $A^+$ RNA molecules, and more preferably a population of mRNA molecules) or one or more DNA molecules), particularly those derived from a cell or tissue. In a preferred aspect, a population of mRNA molecules (a number of different mRNA molecules) are used to make a cDNA library according to the present invention.

To make the nucleic acid molecule or molecules complementary to the one or more templates, a primer (e.g., an oligo(dT) primer) and one or more nucleotides are used for nucleic acid synthesis typically in the 3' to 5' direction. Nucleic acid molecules suitable for reverse transcription according to this aspect of the invention include any nucleic acid molecule, particularly those derived from a prokaryotic or eukaryotic cell. Such cells may include normal cells, diseased cells, transformed cells, established cells, progenitor cells, precursor cells, fetal cells, embryonic cells, bacterial cells, yeast cells, animal cells (including human cells), avian cells, plant cells and the like, or tissue isolated from a plant (e.g., corn, tomato, tobacco, potato, soy bean, etc.) or an animal (e.g., human, cow, pig, mouse, sheep, horse, monkey, canine, feline, rat, rabbit, bird, fish, insect, etc.). Such nucleic acid molecules may also be isolated from viruses.

The nucleic acid molecules that are used as templates to prepare cDNA molecules according to the methods of the present invention are preferably obtained from natural sources, such as a variety of cells, tissues, organs or organisms. Cells that may be used as sources of nucleic acid molecules may be prokaryotic (bacterial cells, including but not limited to those of species of the genera Escherichia, Bacillus, Serratia, Salmonella, Staphylococcus, Streptococcus, Clostridium, Chlamydia, Neisseria, Treponema, Mycoplasma, Borrelia, Legionella, Pseudomonas, Mycobacterium, Helicobacter, Erwinia, Agrobacterium, Rhizobium, Xanthomonas and Streptomyces) or eukaryotic (including fungi (especially yeasts), plants, protozoans and other parasites, and animals including insects (particularly Drosophila spp. cells), nematodes (particularly *Caenorhabditis elegans* cells), and mammals (particularly human cells)).

Mammalian somatic cells that may be used as sources of nucleic acids include blood cells (reticulocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, Schwann cells). Mammalian germ cells (spermatocytes and oocytes) may also be used as sources of nucleic acids for use in the invention, as may the progenitors, precursors and stem cells that give rise to the above somatic and germ cells. Also suitable for use as nucleic acid sources are mammalian tissues or organs such as those derived from brain, kidney, liver, pancreas, blood, bone marrow, muscle, nervous, skin, genitourinary, circulatory, lymphoid, gastrointestinal and connective tissue sources, as well as those derived from a mammalian (including human) embryo or fetus.

Any of the above cells, tissues and organs may be normal, diseased, transformed, established, progenitors, precursors, fetal or embryonic. Diseased cells may, for example, include those involved in infectious diseases (caused by bacteria, fungi or yeast, viruses (including AIDS, HIV, HTLV, herpes, hepatitis and the like) or parasites), in genetic or biochemical pathologies (e.g., cystic fibrosis, hemophilia, Alzheimer's disease, muscular dystrophy or multiple sclerosis) or in cancerous processes. Transformed or established animal cell lines may include, for example, COS cells, CHO cells, VERO cells, BHK cells, HeLa cells, HepG2 cells, K562 cells, 293 cells, L929 cells, F9 cells, and the like. Other cells, cell lines, tissues, organs and organisms suitable as sources of nucleic acids for use in the present invention will be apparent to one of ordinary skill in the art.

Once the starting cells, tissues, organs or other samples are obtained, nucleic acid molecules (such as mRNA) may be isolated therefrom by methods that are well-known in the art (See, e.g., Maniatis, T., et al., *Cell* 15:687–701 (1978); Okayama, H., and Berg, P., *Mol. Cell. Biol.* 2:161–170 (1982); Gubler, U., and Hoffman, B. J., *Gene* 25:263–269 (1983); and Message Maker™ mRNA Isolation System available from Life Technologies, Inc.). The nucleic acid molecules thus isolated may then be used to prepare cDNA molecules and cDNA libraries in accordance with the present invention. The cDNA molecules and/or cDNA libraries produced in accordance with the invention are preferably contained in one or more vectors. Such vectors may be introduced into one or more host cells by standard transformation or transfection techniques well known in the art. Preferred host cells include prokaryotic host cells such as cells of the genus Escherichia, particularly *E. coli*.

Enzymes for use in the compositions, methods and kits of the invention include any enzyme having reverse transcriptase activity. Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase (Saiki, R. K., et al., *Science* 239:487–491 (1988); U.S. Pat. Nos. 4,889,818 and 4,965,188), Tne DNA polymerase (WO 96/10640), Tma DNA polymerase (U.S. Pat. No. 5,374,553) and mutants, fragments, variants or derivatives thereof (see, e.g., commonly owned, co-pending U.S. patent application Ser. No. 08/706,702 and Ser. No. 08/706,706, both filed Sep. 9, 1996, which are incorporated by reference herein in their entireties). As will be understood by one of ordinary skill in the art, modified reverse transcriptases and DNA polymerase having RT activity may be obtained by recombinant or genetic engineering techniques that are well-known in the art. Mutant reverse transcriptases or polymerases can, for example, be obtained by mutating the gene or genes encoding the reverse transcriptase or polymerase of interest by site-directed or random mutagenesis. Such mutations may include point mutations, deletion mutations and insertional mutations. Preferably, one or more point mutations (e.g., substitution of one or more amino acids with one or more different amino acids) are used to construct mutant reverse transcriptases or polymerases for use in the invention. Fragments of reverse transcriptases or polymerases may also be obtained by deletion mutation by recombinant techniques that are well-known in the art, or by enzymatic digestion of the reverse transcriptase(s) or polymerase(s) of interest using any of a number of well-known proteolytic enzymes.

Preferred enzymes for use in the invention include those that are reduced or substantially reduced in RNase H activity. Such enzymes that are reduced or substantially reduced in RNase H activity may be obtained by mutating the RNase H domain within the reverse transcriptase of interest, preferably by one or more point mutations, one or more deletion mutations, and/or one or more insertion mutations as described above. By an enzyme "substantially reduced in RNase H activity" is meant that the enzyme has less than about 30%, less than about 25%, less than about 20%, more preferably less than about 15%, less than about 10%, less than about 7.5%, or less than about 5%, and most preferably less than about 5% or less than about 2%, of the RNase H activity of the corresponding wildtype or RNase H$^+$ enzyme such as wildtype Moloney Murine Leukemia Virus (M-MLV), Avian Myeloblastosis Virus (AMV) or Rous Sarcoma Virus (RSV) reverse transcriptases. The RNase H activity of any enzyme may be determined by a variety of assays, such as those described, for example, in U.S. Pat. No. 5,244,797, in Kotewicz, M. L., et al., *Nucl. Acids Res.* 16:265 (1988), in Gerard, G. F., et al., *FOCUS* 14(5):91 (1992), and in U.S. Pat. No. 5,668,005, the disclosures of all of which are fully incorporated herein by reference.

Polypeptides having reverse transcriptase activity for use in the invention may be obtained commercially, for example from Life Technologies, Inc. (Rockville, Md.), Pharmacia (Piscataway, N.J.), Sigma (Saint Louis, Mo.) or Boehringer Mannheim Biochemicals (Indianapolis, Ind.). Alternatively, polypeptides having reverse transcriptase activity may be isolated from their natural viral or bacterial sources according to standard procedures for isolating and purifying natural proteins that are well-known to one of ordinary skill in the art (see, e.g., Houts, G. E., et al., *J. Virol.* 29:517 (1979)). In addition, the polypeptides having reverse transcriptase activity may be prepared by recombinant DNA techniques that are familiar to one of ordinary skill in the art (see, e.g., Kotewicz, M. L., et al., *Nucl. Acids Res.* 16:265 (1988); Soltis, D. A., and Skalka, A. M., *Proc. Natl. Acad. Sci. USA* 85:3372–3376 (1988)).

Preferred polypeptides having reverse transcriptase activity for use in the invention include M-MLV reverse transcriptase, RSV reverse transcriptase, AMV reverse transcriptase, Rous Associated Virus (RAV) reverse transcriptase, Myeloblastosis Associated Virus (MAV) reverse transcriptase and Human Immunodeficiency Virus (HIV) reverse transcriptase, and others described in WO 98/47921 and derivatives, variants, fragments or mutants thereof, and combinations thereof. In a further preferred embodiment, the reverse transcriptases are reduced or substantially reduced in RNase H activity, and are most preferably selected from the group consisting of M-MLV H$^-$ reverse transcriptase, RSV H$^-$ reverse transcriptase, AMV H$^-$ reverse transcriptase, RAV H$^-$ reverse transcriptase, MAV H$^-$ reverse transcriptase and HIV H$^-$ reverse transcriptase, and derivatives, variants, fragments or mutants thereof, and combinations thereof. Reverse transcriptases of particular interest include AMV RT and M-MLV RT, and more preferably AMV RT and M-MLV RT having reduced or substantially reduced RNase H activity (preferably AMV RT $\alpha$H$^-$/BH$^+$ and M-MLV RT H$^-$). The most preferred reverse transcriptases for use in the invention include SUPERSCRIPT™ mutant M-MLV RT, SUPERSCRIPT™ II mutant M-MLV RT, THEROMSCRIPT™ mutant AMV RT and THERMOSCRIPT™ II mutant AMV RT available from Life Technologies, Inc. See generally, WO 98/47921, U.S. Pat. Nos. 5,244,797 and 5,668,005, the entire contents of each of which are herein incorporated by reference.

A variety of DNA polymerases are useful in accordance with the present invention. Such polymerases include, but are not limited to, *Thermus thermophilus* (Tth) DNA polymerase, *Thermus aquaticus* (Taq) DNA polymerase, *Thermotoga neapolitana* (Tne) DNA polymerase, *Thermotoga maritima* (Tma) DNA polymerase, *Thermococcus litoralis* (Tli or VENT™) DNA polymerase, *Pyrococcus furiosis* (Pfu) DNA polymerase, DEEPVENT™ DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, Mycobacterium spp. DNA polymerase (Mtb, Mlep), and mutants, variants and derivatives thereof.

DNA polymerases used in accordance with the invention may be any enzyme that can synthesize a DNA molecule from a nucleic acid template, typically in the 5' to 3' direction. Such polymerases may be mesophilic or thermophilic. Mesophilic polymerases include T4 DNA polymerase, T5 DNA polymerase, T7 DNA polymerase, Kienow fragment DNA polymerase, DNA polymerase III, DNA polymerase I and the like. Thermostable DNA polymerases include Taq, Tne, Tma, Pfu, VENT™, DEEPVENT™, Tth and mutants, variants and derivatives thereof (U.S. Pat. No. 5,436,149; U.S. Pat. No. 5,512,462; WO 92/06188; WO 92/06200; WO 96/10640; Barnes, W. M., *Gene* 112:29–35 (1992); Lawyer, F. C., et al., *PCR Meth. Appl.* 2:275–287 (1993); Flaman, J. -M., et al., *Nucl. Acids Res.* 22(15):3259–3260 (1994)).

DNA polymerases for use in the invention may be obtained commercially, for example from Life Technologies, Inc. (Rockville, Md.), Perkin-Elmer (Branchburg, N.J.), New England BioLabs (Beverly, Mass.) or Boehringer Mannheim Biochemicals (Indianapolis, Ind.).

The present invention is also directed to nucleic acid molecules produced by the methods of the invention, which may be cDNA molecules, especially full-length cDNA molecules, to vectors (particularly expression vectors) comprising these nucleic acid molecules and cDNA molecules and to host cells comprising these nucleic acid molecules, cDNA molecules, and/or vectors.

Recombinant vectors may be produced according to this aspect of the invention by inserting, using methods that are well-known in the art, one or more of the cDNA molecules or nucleic acid molecules prepared according to the present methods into one or more vectors. The vector used in this aspect of the invention may be, for example, a phage or a plasmid vector, and is preferably a plasmid. Preferred are vectors comprising cis-acting control regions to the nucleic acid encoding the polypeptide of interest. Appropriate trans-acting factors may be supplied by the host, supplied by a complementing vector or supplied by the vector itself upon introduction into the host.

Expression vectors useful in the present invention include chromosomal-, episomal- and virus-derived vectors, e.g., vectors derived from bacterial plasmids or bacteriophages, and vectors derived from combinations thereof, such as cosmids and phagemids, and will preferably include at least one selectable marker such as a tetracycline or ampicillin resistance gene for culturing in a bacterial host cell. Prior to insertion into such an expression vector, the cDNA or nucleic acid molecules of the invention should be operatively linked to an appropriate promoter.

Among vectors preferred for use in the present invention include pQE70, pQE60 and pQE-9, available from Qiagen; pBS vectors, Phagescript vectors, Bluescript vectors, pNH8A, pNH16a, pNH18A, pNH46A, available from Stratagene; pcDNA3 available from Invitrogen; pGEX, pTrxfus, pTrc99a, pET-5, pET-9, pKK223-3, pKK233-3, pDR540, pRIT5 available from Pharmacia; and pSPORT1, pSPORT2, pSV.SPORT1, pCMVSPORT6 and pCMVSPORT available from Life Technologies, Inc. Other suitable vectors will be readily apparent to the skilled artisan.

The invention may be used in conjunction with any methods of cDNA synthesis that are well-known in the art (see, e.g., Gubler, U., and Hoffman, B. J., *Gene* 25:263–269 (1983); Krug, M. S., and Berger, S. L., *Meth. Enzymol.* 152:316–325 (1987); Sambrook, J., et al., *Molecular Cloning: A Laboratory Manual*, 2$^{nd}$ ed., Cold Spring Harbor, N.Y.: Cold Spring Harbor Laboratory Press, pp. 8.60–8.63 (1989); PCT US98/19948; and WO 98/51699) to produce cDNA molecules or libraries. Other methods of cDNA synthesis which may advantageously use the present invention will be readily apparent to one of ordinary skill in the art.

Having obtained cDNA molecules or libraries according to the present methods, these cDNAs may be isolated for further analysis or manipulation. Detailed methodologies for purification of cDNAs are taught in the GENETRAPPER™ manual (Life Technologies), which is incorporated herein by reference in its entirety, although alternative standard techniques that are known in the art (see, e.g., Sambrook, J., et al., *Molecular Cloning: A Laboratory Manual*, 2$^{nd}$ ed., Cold Spring Harbor, N.Y.: Cold Spring Harbor Laboratory Press, pp. 8.60–8.63 (1989)) may also be used. The cDNA molecules or libraries produced by the invention may also be further manipulated by standard molecular biology techniques such as two hybrid analysis, cDNA normalization, sequencing and amplification. More particularly, the methods of the invention and the cDNA molecules or libraries produced by such methods may be used in combination with RT-PCR and 5' RACE technology (Life Technologies, Inc.) and differential display.

A variety of inhibitors and binding molecules are suitable for use in the present methods. Included among these inhibitors or binding molecules are antibodies that bind to the above-described polypeptides having reverse transcriptase activity (such as anti-RT antibodies including anti-AMV RT antibodies, anti-M-MLV RT antibodies or anti-RSV RT antibodies) or to cap structure (e.g., anti-cap antibodies), and fragments thereof (such as Fab or F(ab')$_2$ fragments). Such antibodies may be polyclonal or monoclonal, and may be prepared in a variety of species according to methods that are well-known in the art. See, for instance, Sutcliffe, J. G., et al., *Science* 219:660–666 (1983); Wilson et al., *Cell* 37: 767 (1984); and Bittle, F. J., et al., *J. Gen. Virol.* 66:2347–2354 (1985). Antibodies specific for any of the above-described reverse transcriptases or cap structures can be raised against the intact polymerase polypeptide or cap structures or one or more fragments thereof. These polypeptides or cap structures or fragments thereof may be presented together with a carrier protein (e.g., albumin) to an animal system (such as rabbit or mouse) or, if they are long enough (at least about 25 amino acids), without a carrier.

As used herein, the term "antibody" (Ab) may be used interchangeably with the terms "polyclonal antibody" or "monoclonal antibody" (mAb), except in specific contexts as described below. These terms, as used herein, are meant to include intact molecules as well as antibody fragments (such as, for example, Fab and F(ab')$_2$ fragments) which are capable of specifically binding to a polypeptide having reverse transcriptase activity (such as a DNA polymerase or a reverse transcriptase) or cap structures or portions thereof.

The antibodies used in the methods of the present invention may be polyclonal or monoclonal, and may be prepared by any of a variety of methods (see, e.g., U.S. Pat. No. 5,587,287). For example, polyclonal antibodies may be made by immunizing an animal with one or more polypeptides having reverse transcriptase activity or cap structures or portions thereof according to standard techniques (see, e.g., Harlow, E., and Lane, D., *Antibodies: A Laboratory Manual*, Cold Spring Harbor, N.Y.: Cold Spring Harbor Laboratory Press (1988); Kaufman, P. B., et al., In: *Handbook of Molecular and Cellular Methods in Biology and Medicine*, Boca Raton, Fla.: CRC Press, pp. 468–469 (1995)). Alternatively, monoclonal antibodies (or fragments thereof) to be used in the present methods may be prepared using hybridoma technology that is well-known in the art (Kohler et al., *Nature* 256:495 (1975); Kohler et al., *Eur. J. Immunol.* 6:511 (1976); Kohler et al., *Eur. J. Immunol.* 6:292 (1976); Hammerling et al., In: *Monoclonal Antibodies and T-Cell Hybridomas*, New York: Elsevier, pp. 563–681 (1981); Kaufman, P. B., et al., In: *Handbook of Molecular and Cellular Methods in Biology and Medicine*, Boca Raton, Fla.: CRC Press, pp. 444–467 (1995)).

It will be appreciated that Fab, F(ab')$_2$ and other fragments of the above-described antibodies may be used in the methods described herein. Such fragments are typically produced by proteolytic cleavage, using enzymes such as papain (to produce Fab fragments) or pepsin (to produce F(ab')$_2$ fragments). Antibody fragments may also be produced through the application of recombinant DNA technology or through synthetic chemistry.

The invention also provides kits for use in accordance with the invention. Such kits comprise a carrier means, such as a box or carton, having in close confinement therein one or more container means, such as vials, tubes, bottles and the like, wherein the kit may comprise (in the same or separate containers) one or more host cells, one or more reverse transcriptases, one or more reverse transcription inhibitors, one or more cap binding molecules, one or more DNA polymerases, suitable buffers, one or more nucleotides and/or one or more primers (e.g., oligo(dT) for reverse transcription). The kits encompassed by this aspect of the present invention may further comprise additional reagents and compounds necessary for carrying out standard nucleic acid reverse transcription protocols.

It will be readily apparent to one of ordinary skill in the relevant art that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLES

Example 1

Comparison of First Strand cDNA Synthesis With Varying Ratios of Oligo (dT) Primer/mRNA This example compares first strand cDNA synthesis of the MAP4 gene with various ratios of oligo dT primer/starting mRNA. All components are available from Life Technologies, Inc., Rockville, Md., unless specified otherwise.

The master mix for Superscript II reverse transcriptase (SS II RT) was prepared as specified in Table 1 below

TABLE 1

| Component | μl | μl |
| --- | --- | --- |
| 5X SSII RT buffer | 4 | 28 |
| 0.1M DTT | 2 | 14 |
| 10 mM dNTP | 1 | 7 |
| α-$^{32}$P dCTP | 0.5 | 3.5 |
| Water | 1.5 | 10.5 |
| Total volume | 9 | 63 |

The master mix for ThermoScript™ II RT (TS RT) (AMV RT αH$^-$βH$^+$) (see WO 98/47921) was prepared as specified in Table 2 below.

TABLE 2

| Component | μl | μl |
|---|---|---|
| 10X TS II buffer* | 2 | 38 |
| 0.1M DTT | 2 | 38 |
| 10 mM dNTP | 2 | 38 |
| α-$^{32}$P dCTP | 0.5 | 9.5 |
| Rnase OUT (40 u/μl) | 1 | 19 |
| Water | 1.5 | 28.5 |
| Total volume | 9 | 171 |

*10X TS II buffer comprises 50 mM Tris-HCl (pH 8.4), 750 mM KCl, and 75 mM MgCl$_2$.

The master annealing mix was prepared by adding a 5 Kb MAP4 mRNA, oligo(dT)$_{25-30}$ and water to 5 tubes in the amounts specified in Table 3 below.

TABLE 3

| Ratio of oligo (dT)/mRNA Component | 1:1 | 2.5:1 | 5:1 | 10:1 | 50:1 |
|---|---|---|---|---|---|
| | | | Volume (μl) | | |
| MAP4 mRNA (1 μg/μl) | 5 | 5 | 5 | 5 | 5 |
| Oligo (dT)$_{25-30}$ (10 ng/μl) | 2.6 | 6.5 | 13.1 | — | — |
| Oligo (dT)$_{25-30}$ (100 ng/μl) | — | — | — | 2.6 | 13.1 |
| Water | 42.4 | 38.5 | 31.9 | 42.4 | 31.9 |
| Total volume | 50 | 50 | 50 | 50 | 50 |

The mixture was heated at 70° C. for 10 minutes and then chilled on ice for 5 minutes.

Synthesis of first strand cDNA was done by adding 9 μl of the appropriate reverse transcriptase master mix, 10 μl of the master annealing mix and 1 μl of either SS II RT (200 units/ul) or TS II RT (15 units/ul) for a total volume of 20 μl as summarized in Table 4 below.

TABLE 4

| Tube | Reverse Transcriptase | Temperature | Ratio of oligo (dT)$_{25-30}$/mRNA |
|---|---|---|---|
| 1 | SS II | 45° C. | 1 |
| 2 | | | 2.5 |
| 3 | | | 5 |
| 4 | | | 10 |
| 5 | | | 50 |
| 1 | TS II RT | 45° C. | 1 |
| 2 | | | 2.5 |
| 3 | | | 5 |
| 4 | | | 10 |
| 5 | | | 50 |
| 6 | | 50° C. | 1 |
| 7 | | | 2.5 |
| 8 | | | 5 |
| 9 | | | 10 |
| 10 | | | 50 |
| 11 | | 55° C. | 1 |
| 12 | | | 2.5 |
| 13 | | | 5 |
| 14 | | | 10 |
| 15 | | | 50 |

The reactions were incubated for 1 hour at 45° C. for SS II RT and at 45, 50 or 55° C. for TS II RT. The tubes were placed on ice to complete the reaction. 18 μl first stand cDNA of the reaction tube was precipitated and re-suspended in 10 μl of water. 5 μl of the first strand cDNA was mixed with 5 μl of standard loading buffer (60 mM NaOH, 4 mM EDTA, 0.1% bromophenol blue), and loaded onto 1.4% alkaline agarose gel for analysis. These results are shown in FIGS. 1 and 2.

Figure 2:
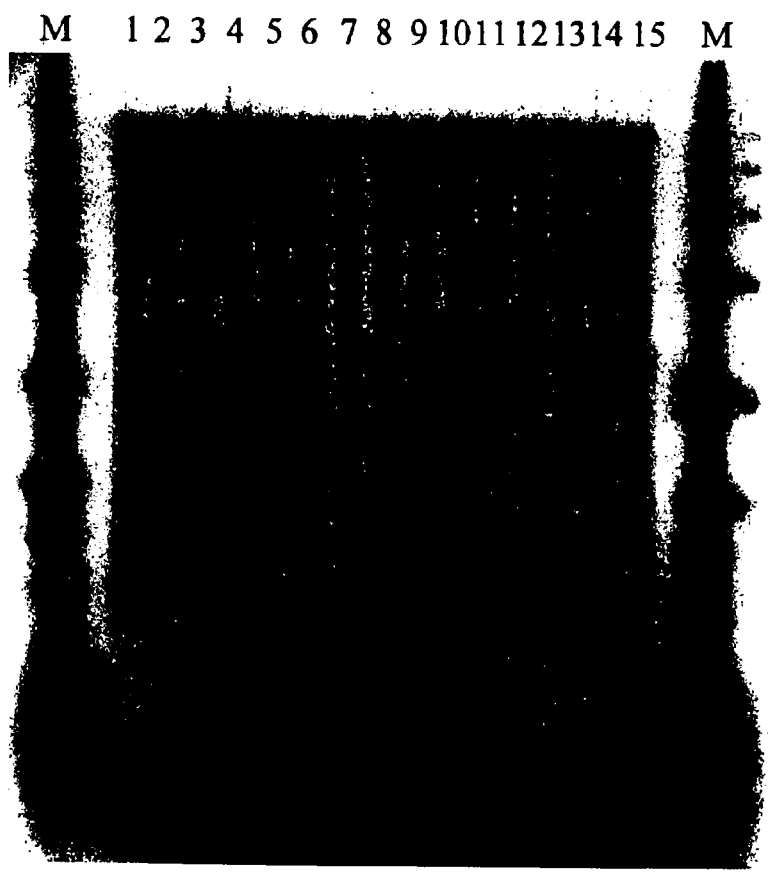
FIG. 2 is an autoradiograph of first strand cDNA synthesized with ThermoScript™ II (TS II) RT at 45° C., 50° C. and 55° C. with a ⅚ Kb template with molar ratios of oligo (dT)$_{25-30}$/mRNA of 1:1, 2.5:1, 5:1, 10:1, and 50:1.

FIG. 1 is an autoradiograph of first strand cDNA synthesized with SS II RT at 45° C. Lane M is the 1 kb DNA ladder. Lanes 1–5 represents reaction conditions with a molar ratio of oligo(dT)$_{25-30}$/mRNA of 1:1, 2.5:1, 5:1, 10:1 and 50:1, respectively. FIG. 2 is an autoradiograph of first strand cDNA synthesized with TS II RT. Lane M is the 1 kb DNA ladder. Lanes 1–5 represent reaction conditions at 45° C. with a molar ratio of oligo(dT)$_{25-30}$/mRNA of 1:1, 2.5:1, 5:1, 10:1 and 50:1, respectively. Lanes 6–10 represent reaction conditions at 50° C. with a molar ratio of oligo (dT)$_{25-30}$/mRNA of 1:1, 2.5:1, 5:1, 10:1 and 50:1, respectively. Lanes 11–15 represent reaction conditions at 55° C. with a molar ratio of oligo (dT)$_{25-30}$/mRNA of 1:1, 2.5:1, 5:1, 10:1 and 50:1, respectively. The results show that by reducing the molar ratio of oligo(dT) primer/mRNA (preferably to 1:1) internal priming with reverse transcriptase was almost entirely eliminated.

Example 2

Comparison of First Strand cDNA Synthesis Under Standard and Hot Start Conditions This experiment was designed to compare first strand cDNA synthesis of the MAP4 gene with standard reaction and hot start conditions.

The annealing mix was prepared by mixing 1 μg of MAP4 mRNA and biotinylated Not I oligo(dT)$_{25}$ primer ((Biotin)$_4$ GACTAGTTCTAGAT CGCGAGCGG CCGCCCTTTTT TTTTTTTTTTTT TTTTTTTT (SEQ ID NO:1); see WO 98/51699) in the desired molar ratio of oligo (dT)/mRNA of 0:1, 1:1 or 15:1 in thin-walled PCR tubes and bringing the volume up to 10 μl with water. If several tubes are identical, they may be made in one batch and aliquotted accordingly. The annealing mix was kept on ice.

The master mix for Superscript II reverse transcriptase (SS II RT) was prepared as specified in Table 5 below.

TABLE 5

| Component | μl | μl |
|---|---|---|
| 5X SSII RT buffer | 4 | 28 |
| 0.1M DTT | 2 | 14 |
| 10 mM dNTP | 1 | 7 |
| α-$^{32}$P dCTP | 0.5 | 3.5 |
| SSII RT (200 u/μl) | 1 | 7 |
| Water | 1.5 | 10.5 |
| Total volume | 10 | 70 |

The SS II RT master mix was then divided into two equal aliquots, one for processing with standard reaction temperatures (batch 1) and one for processing with hot start reaction temperatures (batch 2). To allow for condensation, an additional 10% volume of water was added to batch 2. All mixes were kept on ice.

Synthesis of first strand cDNA was begun by briefly spinning tubes containing annealing mix to collect droplets, placing the tubes in a thermocycler and then heating them to 70° C. for 10 minutes. After this 10 minute cycle at 70° C., the tubes of annealing mix for batch 1 were immediately removed to ice. The tubes of annealing mix for batch 2 were allowed to cool to 45° C. in the thermocycler while the batch 2 master mix was placed in the thermocycler and incubated at 45° C. for 5 minutes. After the 5 minute incubation, 11 μl of the master mix for batch 2 was added to each batch 2 annealing tube and mixed with a pipette 2 times. Care was taken not to spin the tubes to avoid lowering the temperature.

10 μl of the master mix for batch 1 was added to each batch 1 annealing tube. The batch 1 tubes were lightly vortexed and briefly centrifuged to collect condensation droplets. The batch 1 tubes were then returned to the thermocylcer and the tubes from both batch 1 and 2 were incubated at 45° C. for one hour.

5 μl of the first strand cDNA from each tube was mixed with 5 μl of standard loading buffer (60 mM NaOH, 4 mM EDTA, 0.1% bromophenol blue) and loaded onto 1.4% alkaline agarose gel for analysis. The results are shown in FIG. 3.

Figure 3:
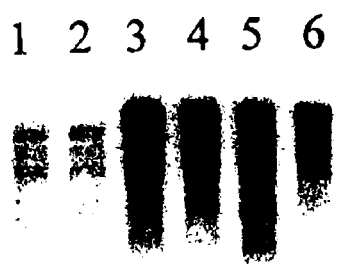
FIG. 3 is an autoradiograph of first strand cDNA synthesized with SS II RT using standard reaction temperatures and varying reaction temperatures with a molar ratio of biotinylated-Not I-oligo(dT)$_{25}$/mRNA of 0:1, 1:1 and 15:1.

FIG. 3 is an autoradiograph of first strand cDNA synthesized with SS II RT. Lanes 1, 3 and 5 represents batch 1 reaction conditions with a molar ratio of biotinylated oligo (dT)/mRNA of 0:1, 1:1 and 15:1, respectively. Lanes 2, 4 and 6 represents batch 2 reaction conditions with a molar ratio of biotinylated oligo(dT)/mRNA of 0:1, 1:1 and 15:1, respectively.

Figure 4:
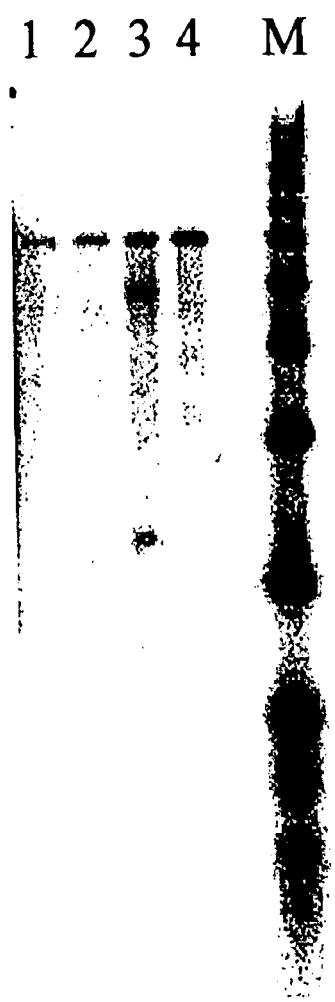
FIG. 4 is an autoradiograph of first strand cDNA synthesized with TS II RT using standard reaction conditions in which the primer/template annealing is incubated on ice prior to cDNA synthesis and using conditions according to the invention in which annealing and the synthesis reaction temperatures are maintained above 30° C. (preferably above 37° C.) with a molar ratio of biotinylated-Not I-oligo(dT)$_{25}$/mRNA of 1:1 and 15:1. Maintaining the annealing and reaction temperatures above 30° C. (preferably above 37° C.) in accordance with the invention may also be referred to as "hot start."

First strand cDNA was also synthesized with TS II RT using 15 units of TS II RT per μg mRNA using a biotinylated oligo(dT)/mRNA ratio of 1:1 and 15:1. The same protocol described above was followed, except that the temperature was varied to 50° C. The results are shown in FIG. 4. FIG. 4 is an autoradiograph of first strand cDNA synthesized with TS II RT. Lane M is the 1 kb DNA ladder. Lanes 1 and 3 represent reactions conditions using standard reaction temperatures at a 1:1 ratio and 15:1 ratio, respectively. Lanes 2 and 4 represent hot start reactions conditions at a 1:1 ratio and 15:1 ratio, respectively, as described above.

The results indicated that by dropping the reaction temperature to the reverse transcriptase reaction temperature after denaturation of the primer and mRNA mixture, the reaction was started directly and internal priming was avoided entirely.

Example 3

Synthesis of Double Strand cDNA by Controlling the Reaction Temperature and the Concentration of Salt and RNase This example describes the synthesis of double stranded cDNA by controlling the reaction temperature and the concentration of salt and different ribonuclease (RNases) during the treatment of the cDNA/mRNA hybrids after first strand cDNA synthesis.

First strand cDNA was synthesized as described above in Example 2 and digested with either RNase I or RNase A as further described below.

RNase I digestion of first strand cDNA was done by re-suspending the first strand cDNA in 180 μl of water and 20 μl of 10× RNase I buffer (100 mM Tris-HCl (pH 7.5), 50 mM EDTA, 2 M sodium acetate). 2.5 units of RNase I (1 unit/μg mRNA) were added and the mixture was mixed well. The RNase I digestion mixture was incubated at 25° C. for 30 minutes and extracted with phenol/chloroform once. The supernatant was precipitated with 1 μl of glycogen, 100 μl of ammonium acetate and 800 μl of ethanol.

RNase A digestion of first strand cDNA was done by re-suspending the first strand cDNA in 200 μl of digestion buffer (10 mM Tris-HCl (pH 7.5), 250 mM NaCl). 12.5 ng of RNase A (5 ng/μg mRNA) were added and the mixture was mixed well. The RNase A digestion mixture was incubated at 25° C. for 30 minutes and extracted with phenol/chloroform once. The supernatant was precipitated with 1 μl of glycogen, 100 μl of ammonium acetate and 800 μl of ethanol.

Example 4

Enrichment of the Full-length cDNA Clones With Cap-binding Proteins

This example describes enrichment of full-length cDNA clones with the cap-binding protein eIF4E.

cDNA was prepared by precipitating the RNase I treated first strand cDNA described in Example 3 above and washing with 70% ethanol. The resulting pellet was dried at room temperature for 5 minutes, and re-suspended in 210 μl of 10 mM KPO$_4$, 100 mM KCl, 2 mM EDTA, 6 mM DTT and 5% glycerol. The cDNA was stored on ice.

eIF4E glutathione sepharose 4B beads were prepared by first mixing glutathione sepharose 4B beads (Pharmacia, Sweden) well. To prepare eIF4E beads, a recombinant host cell expressing GST tagged eIF4E protein (the eIF4E gene was cloned into a GST fusion vector to create a N-terminal GST-eIF4E fusion gene) was grown and the fusion protein was purified by standard techniques. Thus, the invention also relates to recombinant host cells expressing eIF4E protein (particularly as fusion proteins), to vectors comprising the genes expressing such proteins or fusion proteins and to the recombinant proteins or fusion proteins produced. In the present invention any tag can be used (e.g., His Tag, GST tag, HA tag, Trx tag, etc.). Such tags may be positioned at the carboxy and/or N-terminal region of the eIF4E gene.

The GST-eIF4E fusion protein was complexed with sepharose 4B beads by glutathione coupling using gluthionine sepharose 4B beads (Pharmacia Biotech) following the manufacturers protocols. 200 μl of the beads were transferred to a 1.5 ml microcentrifuge tube, centrifuged for 1 second, and 75 μl of supernatant was removed. The beads were washed twice with 1 ml of reaction buffer (10 mM KPO$_4$, 100 mM KCl, 2 mM EDTA, 6 mM DTT and 5% glycerol), and re-suspended in 258 μl of reaction buffer, followed by the addition of 42 μl (18 pmoles/μl) of eIF4E protein (600 pmoles/100 μl beads). The mixture was mixed on a head to head roller at 4° C. for 30 minutes. The mixture was then centrifuged for 1 second, and the supernatant was removed. The beads were washed twice with 1 ml of reaction buffer and once with 1 ml of 25 μg/ml yeast tRNA in reaction buffer. 20 μl of reaction buffer and 5 μg of yeast tRNA were then added to the beads. 200 μl of RNase I treated cDNA was added to the beads, and the content was mixed on a roller at room temperature for 1 hour. After 1 hour, the mixture was centrifuged for 1 second, and the supernatant was removed. The beads were washed twice with 1 ml of reaction buffer and once with 1 ml of 500 μM GDP in reaction buffer. The cDNA was eluted twice with 250 μl of 500 μM GDP in reaction buffer. The eluted solutions were pooled and centrifuged for 1 minute to remove the beads. The eluted cDNA was extracted twice with an equal volume of phenol/chloroform. The cDNA was divided into two tubes and precipitated with 1 μl of glycogen, 0.5 volume of 7.5 M ammonium acetate and 2.5 volume of ethanol.

Example 5

Evaluation of the cDNA Library

To evaluate the quality of the cDNA libraries constructed with the above-described full-length methods, the MAP4 gene (5–6 kb) and other genes was selected as the target genes. MAP4 and other cDNA clones were isolated from libraries constructed by standard methods well-known in the art (see SuperScript™ Plasmid Manual, Life Technologies, Inc.) and the above-described full-length methods with 3' and 5' GeneTrapper cDNA Positive Selection System (Life Technologies, Inc., Rockville, Md.). The positive clones were size analyzed by PCR. Tables 6 and 7 below summarizes the results of the enrichment of full-length cDNA clones in human fibroblast cDNA libraries constructed with methods well-known in the art (control) and the full-length methods described above (full-length method).

TABLE 6

| Gene | % full-length with 5' GeneTrapper | | % full-length with 3' GeneTrapper | |
|---|---|---|---|---|
| | control* | full-length method | control* | full-length method |
| MAP4 (5–6 kb) | 12.8 | 90.3 | 6.25 | 37.5 |

The control library was constructed with SS II RT using known methods.

TABLE 7

| Gene name | Full-length of gene (Kb) | % Full-length by 5' GeneTrapper |
|---|---|---|
| MAP4 (Microtubule-associated protein 4) | 5/6 | 90.3 |
| α-Adaptin* | 3.8/5.7 | 90.0 |
| TR (Transferrin receptor) | 5.0 | 45.0 |
| PTK (Protein tyrosine Kinase) | 3.0 | 84.4 |
| RPA (DNA Replication protein A) | 1.4 | 98.0 |

*There are two members of the genes, 3.8 kb and 5.7 kb in the family.

These results show that the full-length methods described above yielded >90% full-length cDNA clones with the 5' GeneTrapper system, compared to <13% using standard methods. Furthermore, the above-described full-length methods yielded >37% full-length clones with the 3' GeneTrapper system, as compared to <7% using standard methods.

Example 6

First Strand cDNA Synthesis, RNase I Digestion and eIF-4E Capture

All conditions and parameters described above in Examples 2, 3 (RNase I) and 4 were followed, except for the following: 4 reactions of 10 µg of human fibroblast cytoplasmic mRNA were used per reaction (see WO 98/45311); the biotinylated primer-adapter (Biotin)$_4$-GACTAGTTCTAGATCGCGAGCGGCCGCCC(T)$_{25}$ (SEQ ID NO:1) was used at a 1:1 primer/mRNA molar ratio; TS II RT was used at 50° C.; and SS II RT was used at 45° C. Table 8 below summarizes the first strand cDNA and eIF-4E capture results.

Example 7

Second Strand cDNA Synthesis

Second strand cDNA was synthesized by first dissolving each of the four reaction pellets obtained in Example 6 above in 104 µl of DEPC-treated water and then adding the following reagents to each reaction:
4 µl of 5× First Strand Buffer*
30 µl of 5× Second Strand Buffer*
2 µl of 0.1 M DTT
4 µl of 10 mM dNTPs
1 µl of E. coli DNA ligase (10 units/µl)
1 µl of E. coli RNAse H (2 units/µl)
4 µl of E. coli DNA polymerase (10 units/µl)
see SuperScript Plasmid System manual (Life Technologies, Inc., Rockville, Md.).

These reactions mixtures were then incubated for 2 hours at 16° C. 2 µl of T4 DNA polymerase (5 units/µl) was added and incubation at 16° C. was continued for 5 more minutes.

Example 8

Streptavidin Bead Preparation

During the last 30 minutes of the 2 hour second strand reaction described in Example 7 above, streptavidin paramagnetic beads were prepared as follows.

Streptavidin paramagnetic beads (Seradyn) were gently mixed by pipetting until the beads were completely re-suspended. 150 µl of the mixed beads were transferred to the bottom of a microcentrifuge tube for each reaction. The tubes were inserted into a Magna-Sep Magnetic Particle Separator (Life Technologies, Inc., Rockville, Md.) (the magnet) and let sit for 2 minutes. While the tubes were in the magnet, the supernatant was removed by pipetting and 100 µl of TE buffer (10 mM Tris-HCl (pH 7.5), 1 mM EDTA) was immediately added to the beads.

The tubes were then removed from the magnet and the beads were gently re-suspended by finger tapping or vortexing at the lowest setting. The tubes were re-inserted into the magnet After 2 minutes, the supernatant was removed, the beads were re-suspended in 160 µl of binding buffer (10 mM Tris-HCl (pH 7.5), 1 mM EDTA, 1 M NaCl) and the tubes were placed into a microcentrifuge tube rack.

Example 9

Capture of the Double-stranded cDNA Library

After incubating the second strand reaction with T4 DNA polymerase as described in Example 7 above, the reaction mixtures were placed on ice and 10 µl of 0.5 M EDTA was added. Then the cDNA library was captured according to the following procedure (see generally WO 98/51699).

The paramagnetic beads prepared according to Example 8 were transferred to the second strand reaction mixture tubes and gently mixed by pipetting and the suspension was incubated for 60 minutes at room temperature. The tubes were then inserted into the magnet. After 2 minutes, the supernatant was removed and discarded.

100 µl of wash buffer (10 mM Tris-HCl (pH 7.5), 1 mM EDTA, 500 mM NaCl) was added to the beads, the beads were re-suspended by finger tapping or gently vortexing at the lowest setting and the tubes were re-inserted into the magnet for 2 minutes. The supernatant was removed and discarded. This washing step was repeated one more time and then 100 µl of wash buffer was added to the beads. The tubes were then again inserted into the magnet for 5 minutes.

Example 10

Not I Digestion

After the 5 minute incubation described in the last step of Example 9, the supernatant was removed and discarded from the paramagnetic beads and 41 µl of autoclaved, distilled water, 5 µl of REact 3 buffer, 4 µl of Not I was added and the beads were mixed well by pipetting. The reaction was then incubated for 2 hours at 37° C. The tubes were then inserted into the magnet for 2 minutes and the supernatant containing the cDNA library was transferred to fresh tubes.

50 µl of phenol:chloroform:isoamyl alcohol (25:24:1) was added to the supernatant, the solution was vortexed thoroughly, and then centrifuged at room temperature for 5 minutes at 14,000× g. 45 µl of the upper, aqueous layer was carefully removed and transferred to fresh microcentrifuge tubes. 23 µl of 7.5 M ammonium acetate, 1 µl of glycogen (20 µg) and 172 µl of ethanol (−20° C.) was added. The solution was mixed well and stored on dry ice (or −70° C. freezer) for 15 min.

The ethanol solution was then centrifuged at 4° C. for 30 minutes at 14,000× g. The supernatant was carefully removed from the small pellets. 100 µl of 70% ethanol was added and the tubes were centrifuged at room temperature for 2 minutes at 14,000× g. The ethanol was removed and the pellets were dried in a speed-vac for 2 minutes or until dry. The pellets were then dissolved in 20 µl of TE buffer (10 mM Tris-HCl (pH 7.5), 0.1 mM EDTA). The final yield of cDNA was determined by the Cerenkov counts (see Table 8 below).

TABLE 8

| Reverse Transcriptase | standard (S) or varied (V) temperature | % Incorporation (ng of cDNA) | Amount of cDNA after eIF-4E capture |
|---|---|---|---|
| TS II RT | S | 27% (2,720 ng) | 512 ng |
| TS II RT | V (hot start) | 26% (2,640 ng) | 473 ng |
| SS II RT | S | 46% (4,560 ng) | 306 ng |
| SS II RT | V (hot start) | 47% (4,730 ng) | 363 ng |

Example 11

Ligation of cDNA to the Vector and Introduction into E. coli

From 10 to 30 ng of the un-fractionated or size fractionated (≧1.5 kb by low melting gel electrophoresis) cDNA was ligated into a vector pCMVSPORT 6 (Life Technologies, Inc.). This ligation was introduced into E. coli by electroporation as described in the SuperScript Plasmid System manual (Life Technologies, Inc., Rockville, Md.), except that the cloning vector was pre-digested with Not I and Eco RV.

Sequence analysis of randomly selected clones from the cDNA library constructed (304 clones) were analyzed by 5' and 3' sequencing to determine the total percentage of full-length random clones in the cDNA library. Sequences were compared for homology with GeneBank sequences. The results are summarized in Table 9 below. Based on the results, approximately 68% of the random clones were full-length (including known full-length clones and unknown full-length clones). Thus, approximately 17% unknown full-length clones were obtained from the human fibroblast cytoplasmic mRNA library.

TABLE 9

|  | Number of Clones | Percentage |
|---|---|---|
| Total Sequences | 304 | 73.3% |
| Sequences with Homology | 223 | 51% |
| Full-Length Clones | 114 | 17% |
| Potentially Full-Length | 39 | 17% |
| Partial Clones | 70 | 31% |

Example 12

RNAse Assay

First strand cDNA was treated with RNase A at 1000 ng/µg mRNA in TE buffer (10 mM Tris-HCl (pH 7.5), 1 mM EDTA) and RNase I 25 to 40 u/µg mRNA in TEN (10 mM Tris-HCl (pH 7.5), 5 mM EDTA (pH 8.0), 200 mM Sodium Acetate) at 37° C. essentially as described in Example 3. However, this treatment with large amounts of RNase at elevated temperatures resulted in libraries containing very small average cDNA insert size (about 200 bp). Therefore, a second strand cDNA assay was developed to determine the optimal amount of RNase needed.

First strand cDNA (radioactively labeled and non-radioactively labeled) was synthesized using HeLa mRNA at 500 ng of RNA/reaction. The first strand cDNA was precipitated with ethanol and dissolved in DEPC-treated water. The cold first strand cDNA was added to RNase buffer with different amounts of RNase. After incubation for 30 minutes at 25° C., the treated cDNA was extracted with phenol:chloroform and precipitated with ethanol. The treated cDNA was dissolved in DEPC-treated water, a second strand cDNA reaction was performed with $^{32}$P-dCTP plus and minus RNase H. The reaction was extracted with phenol:chloroform and precipitated with ethanol. Equal amounts of cpm was electrophoresed into a 1.4% alkaline-agarose gel. The results are shown in FIGS. 5 and 6.

Figure 5:
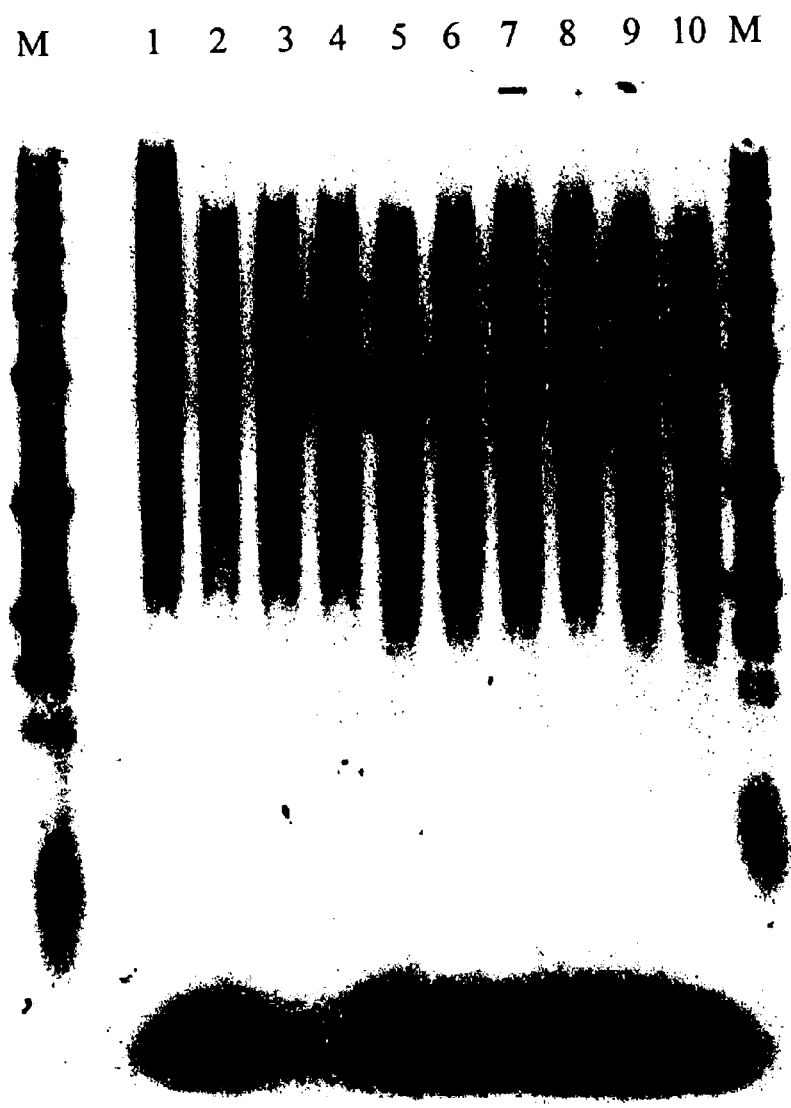
FIG. 5 is an autoradiograph of second strand cDNA synthesized using different amounts of RNase A.

FIG. 5 is an autoradiograph of second strand cDNA synthesized using different amounts of RNase A. Lane M is the 1 kb DNA ladder. Lane 1 represents untreated first strand cDNA. Lane 2 represents untreated second strand cDNA. Lanes 3, 5, 7 and 9 represent second strand cDNA synthesized without RNase H and with RNase A concentrations of 0, 1.25 ng, 2.5 ng and 5 ng, respectively. Lanes 4, 6, 8 and 10 represent second strand cDNA synthesized with RNase H and with RNase A at concentrations of 0, 1.25 ng, 2.5 ng and 5 ng, respectively.

Figure 6:
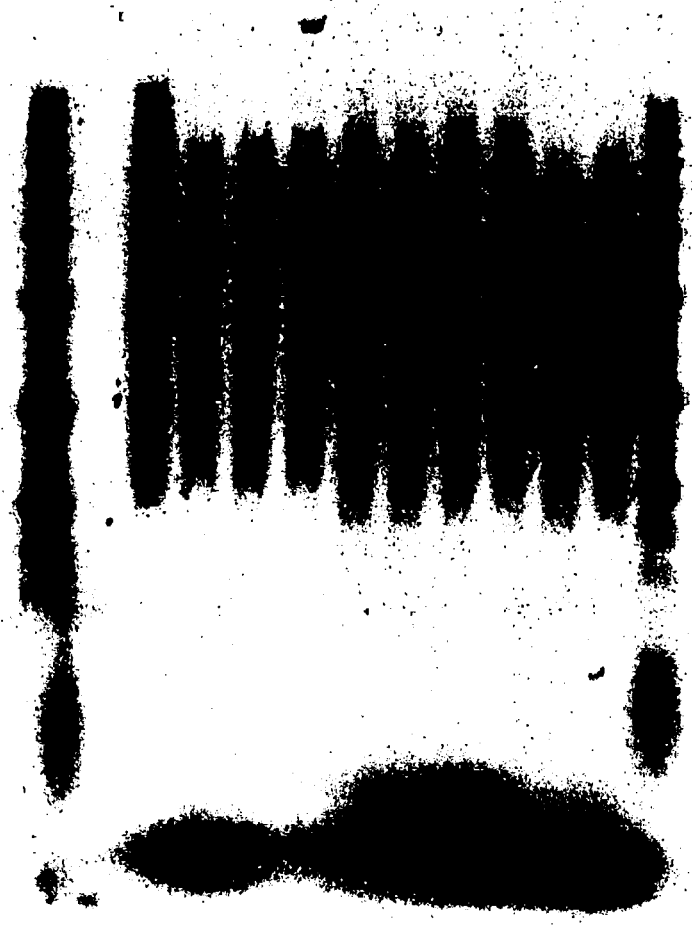
FIG. 6 is an autoradiograph of second strand cDNA synthesized using different amounts of RNase I.

FIG. 6 is an autoradiograph of second strand cDNA synthesized using different amounts of RNase I. Lane M is the 1 kb DNA ladder. Lane 1 represents untreated first strand cDNA. Lane 2 represents untreated second strand cDNA. Lanes 3, 5, 7 and 9 represent second strand cDNA synthesized without RNase H and with RNase I concentrations of 0, 0.5 u, 1.25 u and 2.5 u, respectively. Lanes 4, 6, 8 and 10 represent second strand cDNA synthesized with RNase H and with RNase I at concentrations of 0, 0.5 u, 1.25 u and 2.5 u, respectively.

These gel analysis demonstrated that a concentration of 1.25 ng of RNAse A (see FIG. 5) or 0.5 units of RNAse I (see FIG. 6) may be optimal to use with 500 ng of starting mRNA.

Example 13

Preparation of Antibodies Against Cap Structure

The antibody to cap was generated using m7guanosnine-KLH as the antigen. 1200 hybridomas were plated and only 120 colonies were generated. Of these only 6 colonies were positive for cap. After further analysis, 3 were determined to have the affinity required. The first screen ELISA consists of binding m7guanosine-BSA to an ELISA plate, block with BSA, bind hybridoma supernatants, react with secondary antibody and determine positives via a calorimetric reaction with BCIP/NPT. The secondary screen included incubating appropriate dilutions of the hybridoma supernatants with either 0.1 mM m7GTP, 0.1 mM cap analog M$^7$G$^5$'ppp$^5$'G, 0.5 mM m7guanosine or 0.5 mM GTP. The pretreated supernatant was then used in the standard ELISA procedure The GTP did not compete with the m7guanosine-BSA whereas the m7 versions all competed efficiently.

Having now fully described the present invention in some detail by way of illustration and example for purposes of

What is claimed is:

1. A method for synthesizing one or more cDNA molecules comprising combining one or more mRNA templates, or one or more poly A RNA templates and a primer with at least one polypeptide having reverse transcriptase activity and an antibody or antibody fragment inhibitor of the polypeptide having reverse transcriptase activity, incubating said template, primer, polypeptide and inhibitor at a temperature between 10° C. and 90° C., wherein said inhibitor inhibits said reverse transcriptase activity at said temperature; and elevating the temperature of said template, primer, polypeptide and inhibitor thereby inactivating said inhibitor, whereby one or more cDNA molecules are synthesized.

2. The method of claim 1, wherein said antibody or antibody fragment is polyclonal or monoclonal.

3. The method of claim 1, wherein said polypeptide is a reverse transcriptase selected from the group consisting of Moloney Murine Leukemia Virus reverse transcriptase (M-MLV RT), Rous Sarcoma Virus reverse transcriptase (RSV RT), Avian myeloblastosis Virus reverse transcriptase (AMV RT), Rous associated Virus reverse transcriptase (RAV RT), Myeloblastosis associated virus reverse transcriptase (MAV RT) and Human Immunodeficiency Virus reverse transcriptase (HIV RT), and fragments thereof having reverse transcriptase activity.

4. The method of claim 3, wherein said reverse transcriptase is reduced in RNase H activity.

5. The method of claim 4, wherein said RNase H activity is reduced to less than about 30% of RNase H activity of a corresponding wildtype reverse transcriptase.

6. The method of claim 1, wherein said inhibitor inhibits, prevents, or reduces internal priming.

7. The method of claim 6, wherein said temperature is within the range of about 10–65° C.

8. The method of claim 6, wherein said temperature is within the range of about 10–55° C.

9. The method of claim 6, wherein said temperature is within the range of about 10–45° C.

10. The method of claim 6, wherein said temperature is within the range of about 10–35° C.

11. The method of claim 1, wherein the primer to template ratio is between 12:1 and 1:12.

12. The method of claim 11, wherein said primer to template ratio is between 10:1 and 1:10.

13. The method of claim 11, wherein said primer to template ratio is between 5:1 and 1:5.

14. The method of claim 1, wherein said primer has a length of between 20 and 100 bases.

15. The method of claim 14, wherein said length is between 20 and 75 bases.

16. The method of claim 14, wherein said length is between 20 and 50 bases.

17. The method of claim 14, wherein said length is between 25 and 35 bases.

18. The method of claim 1, wherein said polypeptide is a retroviral reverse transcriptase.

19. The method of claim 1, wherein said polypeptide is a reverse transcriptase selected from the group consisting of M-MLV RT, RSV RT and AMV RT.

20. The method of claim 19, wherein said reverse transcriptase is a M-MLV RT having and RNase H activity less than about 30% of the RNase H activity of the corresponding wildtype M-MLV RT.

21. Then method of claim 19, wherein said reverse transcriptase is selected from the group consisting of SUPERSCRIPT™ (mutant M-MLV RT having reduced RNase H activity), SUPERSCRIPT™ II (mutant M-MLV RT having reduced RNase H activity), THERMOSCRIPT™ (mutant AMV RT having reduced RNase H activity) and THERMOSCRIPT™ II (mutant AMV RT having reduced RNase H activity).

22. The method of claim 1, wherein said one or more mRNA templates is a population of mRNA templates suitable for the production of a cDNA library.

23. The method of claim 1, wherein said cDNA molecules are a cDNA library.

24. The method of claim 1, wherein said primer is an oligo(dT) primer.

* * * * *